(12) United States Patent
Eek

(10) Patent No.: US 12,128,088 B2
(45) Date of Patent: *Oct. 29, 2024

(54) TREATMENT OF CONNECTIVE TISSUE INJURIES

(71) Applicant: Bjorn Eek, Lake Forest, CA (US)

(72) Inventor: Bjorn Eek, Lake Forest, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/470,720

(22) Filed: Sep. 20, 2023

(65) Prior Publication Data

US 2024/0009273 A1    Jan. 11, 2024

Related U.S. Application Data

(63) Continuation of application No. 17/653,209, filed on Mar. 2, 2022, which is a continuation-in-part of application No. 17/472,366, filed on Sep. 10, 2021, now Pat. No. 11,298,406.

(51) Int. Cl.
| | | |
|---|---|---|
| *A61K 38/18* | (2006.01) | |
| *A61K 9/00* | (2006.01) | |
| *A61K 31/7008* | (2006.01) | |
| *A61K 31/726* | (2006.01) | |

(52) U.S. Cl.
CPC ........ *A61K 38/1841* (2013.01); *A61K 9/0019* (2013.01); *A61K 31/7008* (2013.01); *A61K 31/726* (2013.01)

(58) Field of Classification Search
CPC .................................................. A61K 38/1841
See application file for complete search history.

(56) References Cited

U.S. PATENT DOCUMENTS

| | | | |
|---|---|---|---|
| 5,837,258 | A | 11/1998 | Grotendorst |
| 6,149,916 | A | 11/2000 | Grotendorst et al. |
| 7,744,651 | B2 | 6/2010 | Trieu et al. |
| 2007/0227547 | A1 | 10/2007 | Trieu |
| 2008/0103564 | A1 | 5/2008 | Burkinshaw et al. |
| 2014/0271870 | A1 | 9/2014 | O'Shaughnessey et al. |
| 2016/0074479 | A1 | 3/2016 | Serbousek et al. |
| 2018/0169137 | A1 | 6/2018 | Erwin |

FOREIGN PATENT DOCUMENTS

| | | |
|---|---|---|
| WO | 96/38168 A1 | 12/1996 |
| WO | 2001066130 A1 | 9/2001 |
| WO | 2007136673 A2 | 11/2007 |
| WO | 2008012511 A1 | 1/2008 |
| WO | 2014149270 A1 | 9/2014 |
| WO | 2017075719 A1 | 5/2018 |

OTHER PUBLICATIONS

Extended European Search Report of European Application No. 23159317.9 issued on May 6, 2023.
Li et al. "Action of fibroblast growth factor-2 on the intervertebral disc", Arthritis Research & Therapy vol. 10 No. 2.
Bao-Gan Peng, "Pathophysiology, diagnosis, and treatment of discogenic low back pain", WJO www.wjgnet.com, Apr. 18, 2013 vol. 4, Issue 2.
Zhang et al. "Toxicity Effects of Methylene Blue on Rat Intervertebral Disc Annulus Fibrosus Cells", www.painphysicianjournal.com. Journal Article; (Journal Article), vol. 22, Issue: 2, pp. 155-164.
Riester et al. "RNA sequencing identifies gene regulatory networks controlling extracellular matrix synthesis in intervertebral disk tissues"; Journal of Orthopaedic, vol. 36, Issue: 5, pp. 1356-1369, 2018.
Cleveland Clinic "Connective Tissue Diseases" 7 pages Dec. 16, 2019.
Garrett et al. "Involvement of CTGF in TGF-beta 1-Stimulation of Myofibroblast Differentiation and Collagen Matrix Contraction in the Presence of Mechanical Stress" Investigative Ophthalmology & Visual Science, Apr. 2024, vol. 45, No. 4, 1109-1116 (2004).
Hi Medial Cell Culture "Dulbecco's Modified Eagle Medium(DMEM)" 2 pgs 2011 (2011).

*Primary Examiner* — Thane Underdahl
(74) *Attorney, Agent, or Firm* — Procopio, Cory, Hargreaves & Savitch LLP; Brent A. Johnson; Erica A. Spence

(57) ABSTRACT

This disclosure relates to treating a connective tissue injury. The treatment involves injecting, or otherwise administering, a therapeutic composition into an animal, such as a human being, in need thereof. The therapeutic composition may contain transforming growth factor beta 1 (TGF-β1) and/or transforming growth factor β2 (TGF-β2), connective tissue growth factor (CTGF), and a pharmaceutically acceptable excipient or a secondary agent.

13 Claims, No Drawings

TREATMENT OF CONNECTIVE TISSUE INJURIES

CROSS-REFERENCE TO RELATED APPLICATIONS

This application is a continuation of U.S. patent application Ser. No. 17/653,209, filed Mar. 2, 2022, which is a continuation-in-part of U.S. patent application Ser. No. 17/472,366, filed Sep. 10, 2021, now U.S. Pat. No. 11,298, 406, which is incorporated by reference herein in its entirety.

FIELD

This disclosure relates to therapeutic compositions and methods for treating connective tissue injuries.

BACKGROUND

Connective tissue injuries can occur as a result of a motor vehicle collision, a sports injury, or other trauma. Although connective tissue injuries are common, satisfactory treatment of these injuries is often elusive. Therefore, there is a continuing need for additional treatments for connective tissue injuries.

SUMMARY

Some embodiments include a method of treating a connective tissue injury, comprising injecting a therapeutic composition at, into, or near an injured connective tissue in an animal in need thereof, wherein the therapeutic composition comprises transforming growth factor beta 1 (TGF-β1) and/or transforming growth factor beta 2 (TGF-β2), connective tissue growth factor (CTGF), and a pharmaceutically acceptable excipient or a secondary agent.

Some embodiments include a therapeutic composition comprising TGF-β1 and/or TGF-β2, CTGF, water, and at least 2 of the following excipients or secondary agents: glucosamine, chondroitin, dextrose, an anesthetic, carboxymethyl cellulose, hyaluronic acid, a corticosteroid, and a buffer.

DETAILED DESCRIPTION

Generally, this disclosure involves injecting, or otherwise administering, a therapeutic composition into an animal, such as a human being, who is suffering from a connective tissue injury. Connective tissue injuries commonly affect the musculoskeletal system. Most injuries affect tendon, fascia, ligament, and/or joint capsule at or near the fibro-periosteal junction, the interface between connective tissue and periosteum of bone. The junction is potentially weak and is a common site of injury by tension or shear forces. Blood supply is necessary for repair and is mostly provided by capillaries which are small and delicate in structure. If tissue swelling after injury becomes prolonged or excessive, capillary circulation can become compromised enough to hinder and limit the repair process. Pain and limited function become manifestations of incomplete healing. The best treatment is to reduce swelling and stimulate the repair process. Initially, external treatment by application of heat or cold, and gentle movement can be very helpful in stimulating the repair response.

The therapeutic composition can be administered to a patient for treatment of connective tissue injuries, such as a connective tissue injury to a neck, back, knee, shoulder, elbow, wrist, ankle, hip, hand, foot, etc., including connective tissue injury involving a tendon, fascia, ligament, or a joint capsule. A connective tissue injury may include damage to the connective tissue that is a result of physical trauma, misuse, or overuse of the connective tissue, such as an accident, e.g., a fall, an automobile collision, a sports injury, a repetitive use injury, an overuse injury (e.g. a runner's injury). In some embodiments, the connective tissue injury is not a result of a natural disease such as arthritis. In some embodiments, the connective tissue injury is not a result of arthritis.

For treatment of connective tissue injuries, the therapeutic composition is administered, such as by injection, at or near the injured connective tissue (e.g. within 6 inches, within 5 inches, within 4 inches, within 3 inches, within about 2 inches, within about 1 inch, within about 0.5 inches of, or directly into the injured connective tissue). In some embodiments, the therapeutic composition is administered, such as by injection, at or near (e.g. within 6 inches, within 5 inches, within 4 inches, within 3 inches, within about 2 inches, within about 1 inch, or within about 0.5 inches of, or directly into) a fibro-periosteal junction of tendon, fascia, ligament, or joint capsule, or at or near the interface of (e.g. within 6 inches, within 5 inches, within 4 inches, within 3 inches, within about 2 inches, within about 1 inch, or within about 0.5 inches of, or directly into) the connective tissue to periosteum.

Growth factors derived from notochordal cell media or stem cells, such as transforming growth factor beta 1 (TGF-β1), transforming growth factor beta 2 (TGF-β2), or connective tissue growth factor (CTGF), can have a positive and substantial effect on healing by energizing tissue cells as fibroblasts, to promote collagen and the reparative process.

The therapeutic composition of the present disclosure comprises TGF-β1 (and/or TGF-β2), connective tissue growth factor (CTGF), and a pharmaceutically acceptable excipient or a secondary agent.

In some embodiments, the therapeutic composition comprises transforming growth factor TGF-β1, connective tissue growth factor (CTGF), and a pharmaceutically acceptable excipient or a secondary agent.

Any suitable amount of TGF-β1 may be used in the therapeutic composition, such as at least about 1 ng/mL, at least about 5 ng/mL, at least about 10 ng/mL, about 1-100 ng/mL, about 10-100 ng/mL, about 0.5-40 ng/mL, about 1-20 ng/mL, about 0.5-10 ng/mL, about 10-20 ng/mL, about 20-30 ng/mL, about 30-40 ng/mL, about 40-60 ng/mL, about 60-80 ng/mL, about 80-100 ng/mL, about 0.5-3 ng/mL, about 3-6 ng/mL, about 6-9 ng/mL, about 9-12 ng/mL, about 12-15 ng/mL, about 15-18 ng/mL, about 18-21 ng/mL, about 21-27 ng/mL, about 27-34 ng/mL, or about 34-40 ng/mL. In some embodiments, the concentration of TGF-β1 in the therapeutic composition is about 1-20 ng/mL.

Transforming growth factor beta 2 (TGF-β2) may potentially supplement or replace TGF-β1. Any suitable amount of TGF-β2 may be used in the therapeutic composition, such as at least about 1 ng/mL, at least about 5 ng/mL, at least about 10 ng/mL, about 1-100 ng/mL, about 10-100 ng/mL, about 0.5-40 ng/mL, about 1-20 ng/mL, about 0.5-10 ng/mL, about 10-20 ng/mL, about 20-30 ng/mL, about 30-40 ng/mL, about 40-60 ng/mL, about 60-80 ng/mL, about 80-100 ng/mL, about 0.5-3 ng/mL, about 3-6 ng/mL, about 6-9 ng/mL, about 9-12 ng/mL, about 12-15 ng/mL, about 15-18 ng/mL, about 18-21 ng/mL, about 21-27 ng/mL, about 27-34 ng/mL, or about 34-40 ng/mL. In some embodiments, the concentration of TGF-β1 in the therapeutic composition is about 1-20 ng/mL.

Any suitable amount of CTGF may be used in the therapeutic composition, such as at least about 50 ng/mL, at least about 100 ng/mL, at least about 200 ng/mL, about 20-500 ng/mL, about 50-500 ng/mL, about 20-400 ng/mL, about 50-200 ng/mL, about 10-100 ng/mL, about 50-100 ng/mL, about 100-200 ng/mL, about 20-50 ng/mL, about 50-80 ng/mL, about 80-110 ng/mL, about 110-140 ng/mL, about 140-170 ng/mL, about 170-200 ng/mL, about 200-300 ng/mL, about 300-400 ng/mL, or about 400-500 ng/mL. In some embodiments, the concentration of CTGF in the therapeutic composition is about 50-200 ng/mL.

Suitable pharmaceutically acceptable excipients or secondary agents can include, but are not limited to: 1) dextrose, 2) a local anesthetic such as lidocaine, 3) a chondroitin, 4) a carboxymethyl cellulose, 5) a glucosamine, 6) a hyaluronic acid, and 7) phosphate buffer saline. A pharmaceutical composition may contain at least 1, at least 2, at least 3, at least 4, at least 5, at least 6, at least 7, or all 8 of these pharmaceutically acceptable excipients or secondary agents, as well as others, such as a steroid (e.g. a corticosteroid, such as cortisone, hydrocortisone, prednisone, prednisolone, methylprednisolone, betamethasone, dexamethasone, triamcinolone, etc.).

Dextrose may be useful to stimulate the repair response of injured connective tissue. Dextrose may serve as a mild growth factor stimulating fibroblasts to manufacture collagen, the building block of connective tissue. Any suitable amount of dextrose may be used in the therapeutic composition, such as up to about 25%, about 0-5%, about 0-25%, about 1-2%, about 1-1.5%, about 2-30%, about 5-15%, about 2-10%, about 10-20%, about 20-30%, about 2-5%, about 5-10%, about 10-15%, about 5-7%, about 7-9%, about 9-11%, about 11-13%, about 13-15%, about 15-18%, about 18-21%, or about 21-25% by weight of the therapeutic composition. In some embodiments, the dextrose is about 5-15% of the therapeutic composition. In some embodiments, the dextrose is about 10-25% of the therapeutic composition.

A local anesthetic may be useful to stimulate the repair response of injured connective tissue. Local anesthetic may have an immediate anesthetic effect, and may also help to repolarize unmyelinated nerve fibers, including sensory and sympathetic nerve fibers. This may reduce pain. This may also help to reflexly reduce muscle spasm, which may in turn ease muscle tension about the injury site and promote circulation. The therapeutic composition may an anesthetic such as procaine, chloroprocaine, prilocaine, tetracaine, cinchocaine, ropivacaine, etc. The local anesthetic may be present in a free base form and/or any suitable salt form.

In some embodiments, the local anesthetic includes lidocaine or bupivacaine, including lidocaine free base and/or any suitable salt form, such as a hydrochloride salt, or bupivacaine free base and/or any suitable salt form, such as a hydrochloride salt. Any suitable amount of lidocaine or bupivacaine (in a free base and/or a salt form, such as a hydrochloride salt) may be used in the therapeutic composition, such as about 0.1-2%, about 0.25-1%, about 0.1-0.25%, about 0.25-0.3%, about 0.3-0.4%, about 0.4-0.5%, about 0.5-0.6%, about 0.6-0.7%, about 0.7-0.8%, about 0.8-0.9%, about 0.9-1%, about 0.25-0.5%, about 0.5-0.75%, about 0.75-1%, about 1-1.5%, or about 1.5-2% by weight of the therapeutic composition. In some embodiments, the lidocaine is about 0.25-1% of the therapeutic composition.

The therapeutic composition may contain a chondroitin, including a chondroitin in an amine form and/or a salt form, such as a sulfate salt. Any suitable amount of the chondroitin (in an amine and/or a salt form, such as a sulfate salt), may be used in the therapeutic composition, such as about 0.2-4%, about 0.1-0.5%, about 0.1-1%, about 0.1-2%, about 0.5-2%, about 0.2-0.5%, about 0.5-0.8%, about 0.8-1.1%, about 1.1-1.4%, about 1.4-1.7%, about 1.7-2%, about 0.5-1%, about 1-1.5%, about 1.5-2%, about 2-2.5%, about 2.5-3%, about 3-3.5%, or about 3.5-4% by weight of the therapeutic composition. In some embodiments, the chondroitin, e.g., chondroitin sulfate, is about 0.5-2% of the therapeutic composition.

The therapeutic composition may contain carboxymethyl cellulose, including carboxymethyl cellulose in an acid form and/or a salt form, such as a sodium salt. Any suitable amount of the carboxymethyl cellulose (in an acid and/or a salt form, such as a sodium salt), may be used in the therapeutic composition, such as about 0.01-5%, about 0-0.5%, about 0.01-0.25%, about 0.25-0.5%, about 0.5-1%, about 1-2%, about 2-3%, about 3-4%, or about 4-5% by weight of the therapeutic composition. In some embodiments, the carboxymethyl cellulose, is about 0.01-0.25% of the therapeutic composition.

The therapeutic composition may contain glucosamine, including glucosamine in an amine form and/or a salt form, such as a hydrochloride (HCl) salt. Any suitable amount of the glucosamine (in an amine and/or a salt form, such as a hydrochloride salt (e.g., glucosamine HCl)), may be used in the therapeutic composition, such as about 1-25%, about 1-10%, about 5-25%, about 5-20%, about 0.5-12%, about 1-5%, about 1-6%, about 0.5-1%, about 1-1.5%, about 1-2%, about 2-3%, about 3-4%, about 4-5%, about 5-6%, about 6-8%, about 8-10%, about 10-12%, about 5-20% by weight of the therapeutic composition. In some embodiments, the glucosamine, e.g., glucosamine HCl, is about 1-6% of the therapeutic composition.

The therapeutic composition may contain hyaluronic acid, including hyaluronic acid in an acid form and/or a salt form, such as a sodium salt. Any suitable amount of the hyaluronic acid (in an acid and/or a salt form, such as a sodium salt), may be used in the therapeutic composition, such as about 0.02-12%, about 0.05-6%, about 0.02-1%, about 1-2%, about 2-3%, about 3-4%, about 4-5%, about 5-6%, about 6-8%, about 8-10%, or about 10-12% by weight of the therapeutic composition. In some embodiments, the hyaluronic acid is about 0.05-6% of the therapeutic composition.

The therapeutic composition may contain a suitable buffer, such as a phosphate buffer. A phosphate buffer may include $PO_4^{3-}$, $HPO_4^{2-}$, $H_2PO_4^-$, or a combination thereof, in a ratio appropriate for the pH of interest. In some embodiments, the therapeutic composition is buffered to a pH of about 5-8, about 5-6, about 6-7, or about 7-8. In some embodiments, the therapeutic composition has a pH of about 6-7. In some embodiments, the therapeutic composition has a pH of about 7-8. In some embodiments, the therapeutic composition has a pH of about 7.4. In some embodiments, the therapeutic composition contains phosphate buffer saline.

The therapeutic composition may contain water, including sterile water, normal saline, or phosphate buffer saline in an amount sufficient to provide the concentrations listed above for the other ingredients. For example, the water, saline, or phosphate buffer saline may be about 60-95% of the therapeutic composition.

The therapeutic composition may include other ingredients, such as dimethyl sulfoxide (e.g. up to about 15%, up to 10%, or up to 5%).

In some embodiments, the therapeutic composition comprises dextrose. In some embodiments, the therapeutic composition comprises a local anesthetic such as lidocaine (either in a free base form or a salt form). In some embodiments, the therapeutic composition comprises chondroitin (e.g., in a salt form, such as a sulfate salt, or a free base form). In some embodiments, the therapeutic composition comprises carboxymethyl cellulose (e.g., in an acid form or a salt form, such as a sodium salt). In some embodiments, the therapeutic composition comprises glucosamine (e.g., in a free base or a salt form, such as an HCl salt). In some embodiments, the therapeutic composition comprises hyaluronic acid (e.g., in an acid form or a salt form, such as a sodium salt). In some embodiments, the therapeutic composition comprises a phosphate buffer. In some embodiments, the therapeutic composition comprises water, saline, or phosphate buffer saline.

In some embodiments, the therapeutic composition comprises TGF-β1, CTGF, dextrose and a local anesthetic such as lidocaine (either in a free base form or a salt form). In some embodiments, the therapeutic composition comprises TGF-β1, CTGF, dextrose and chondroitin (e.g., in a salt form, such as a sulfate salt, or a free base form). In some embodiments, the therapeutic composition comprises TGF-β1, CTGF, dextrose and carboxymethyl cellulose (e.g., in an acid form or a salt form, such as a sodium salt). In some embodiments, the therapeutic composition comprises TGF-β1, CTGF, dextrose and glucosamine (e.g., in a free base or a salt form, such as an HCl salt). In some embodiments, the therapeutic composition comprises TGF-β1, CTGF, dextrose and hyaluronic acid (e.g., in an acid form or a salt form, such as a sodium salt). In some embodiments, the therapeutic composition comprises TGF-β1, CTGF, dextrose and phosphate buffer saline. In some embodiments, the therapeutic composition comprises TGF-β1, CTGF, dextrose and water or saline. In some embodiments, the therapeutic composition comprises TGF-β1, CTGF, a local anesthetic such as lidocaine (either in a free base form or a salt form), and chondroitin (e.g., in a salt form, such as a sulfate salt, or a free base form). In some embodiments, the therapeutic composition comprises TGF-β1, CTGF, a local anesthetic such as lidocaine (either in a free base form or a salt form), and carboxymethyl cellulose (e.g., in an acid form or a salt form, such as a sodium salt). In some embodiments, the therapeutic composition comprises TGF-β1, CTGF, a local anesthetic such as lidocaine (either in a free base form or a salt form), and glucosamine (e.g., in a free base or a salt form, such as an HCl salt). In some embodiments, the therapeutic composition comprises TGF-β1, CTGF, a local anesthetic such as lidocaine (either in a free base form or a salt form), and hyaluronic acid (e.g., in an acid form or a salt form, such as a sodium salt). In some embodiments, the therapeutic composition comprises TGF-β1, CTGF, a local anesthetic such as lidocaine (either in a free base form or a salt form), and phosphate buffer saline. In some embodiments, the therapeutic composition comprises TGF-β1, CTGF, a local anesthetic such as lidocaine (either in a free base form or a salt form), and water or saline. In some embodiments, the therapeutic composition comprises TGF-β1, CTGF, chondroitin (e.g., in a salt form, such as a sulfate salt, or a free base form) and carboxymethyl cellulose (e.g., in an acid form or a salt form, such as a sodium salt). In some embodiments, the therapeutic composition comprises TGF-β1, CTGF, hyaluronic acid (e.g., in an acid form or a salt form, such as a sodium salt) and phosphate buffer saline. In some embodiments, the therapeutic composition comprises TGF-β1, CTGF, hyaluronic acid (e.g., in an acid form or a salt form, such as a sodium salt) and water or saline.

In some embodiments, the therapeutic composition comprises TGF-β1, CTGF, chondroitin (e.g., in a salt form, such as a sulfate salt, or a free base form) and glucosamine (e.g., in a free base or a salt form, such as an HCl salt). In some embodiments, the therapeutic composition comprises TGF-β1, CTGF, chondroitin (e.g., in a salt form, such as a sulfate salt, or a free base form) and hyaluronic acid (e.g., in an acid form or a salt form, such as a sodium salt). In some embodiments, the therapeutic composition comprises TGF-β1, CTGF, chondroitin (e.g., in a salt form, such as a sulfate salt, or a free base form) and phosphate buffer saline. In some embodiments, the therapeutic composition comprises TGF-β1, CTGF, chondroitin (e.g., in a salt form, such as a sulfate salt, or a free base form) and water or saline. In some embodiments, the therapeutic composition comprises TGF-β1, CTGF, carboxymethyl cellulose (e.g., in an acid form or a salt form, such as a sodium salt) and glucosamine (e.g., in a free base or a salt form, such as an HCl salt). In some embodiments, the therapeutic composition comprises TGF-β1, CTGF, carboxymethyl cellulose (e.g., in an acid form or a salt form, such as a sodium salt) and hyaluronic acid (e.g., in an acid form or a salt form, such as a sodium salt). In some embodiments, the therapeutic composition comprises TGF-β1, CTGF, carboxymethyl cellulose (e.g., in an acid form or a salt form, such as a sodium salt) and phosphate buffer saline. In some embodiments, the therapeutic composition comprises TGF-β1, CTGF, carboxymethyl cellulose (e.g., in an acid form or a salt form, such as a sodium salt) and water or saline. In some embodiments, the therapeutic composition comprises TGF-β1, CTGF, glucosamine (e.g., in a free base or a salt form, such as an HCl salt) and hyaluronic acid (e.g., in an acid form or a salt form, such as a sodium salt). In some embodiments, the therapeutic composition comprises TGF-β1, CTGF, glucosamine (e.g., in a free base or a salt form, such as an HCl salt) and phosphate buffer saline. In some embodiments, the therapeutic composition comprises TGF-β1, CTGF, glucosamine (e.g., in a free base or a salt form, such as an HCl salt) and water or saline. In some embodiments, the therapeutic composition comprises TGF-β1, CTGF, phosphate buffer saline and water or saline.

In some embodiments, the therapeutic composition comprises TGF-β1, CTGF, dextrose, a local anesthetic such as lidocaine (either in a free base form or a salt form), and chondroitin (e.g., in a salt form, such as a sulfate salt, or a free base form). In some embodiments, the therapeutic composition comprises TGF-β1, CTGF, dextrose, a local anesthetic such as lidocaine (either in a free base form or a salt form), and carboxymethyl cellulose (e.g., in an acid form or a salt form, such as a sodium salt). In some embodiments, the therapeutic composition comprises TGF-β1, CTGF, dextrose, a local anesthetic such as lidocaine (either in a free base form or a salt form), and glucosamine (e.g., in a free base or a salt form, such as an HCl salt). In some embodiments, the therapeutic composition comprises TGF-β1, CTGF, dextrose, a local anesthetic such as lidocaine (either in a free base form or a salt form), and hyaluronic acid (e.g., in an acid form or a salt form, such as a sodium salt). In some embodiments, the therapeutic composition comprises TGF-β1, CTGF, dextrose, a local anesthetic such as lidocaine (either in a free base form or a salt form), and phosphate buffer saline. In some embodiments, the therapeutic composition comprises TGF-β1, CTGF, dextrose, a local anesthetic such as lidocaine (either in a free base form or a salt form), and water or saline. In some embodiments, the therapeutic composition comprises TGF- β1, CTGF, dextrose, chondroitin (e.g., in a salt form, such as a sulfate salt, or a free base form), and carboxymethyl cellulose (e.g., in an acid form or a salt form, such as a sodium salt). In some embodiments, the therapeutic composition comprises TGF-β1, CTGF, dextrose, chondroitin (e.g., in a salt form, such as a sulfate salt, or a free base form), and glucosamine (e.g., in a free base or a salt form, such as an HCl salt). In some embodiments, the therapeutic composition comprises TGF-β1, CTGF, dextrose, chondroitin (e.g., in a salt form, such as a sulfate salt, or a free base form), and hyaluronic acid (e.g., in an acid form or a salt form, such as a sodium salt). In some embodiments, the therapeutic composition comprises TGF-β1, CTGF, dextrose, chondroitin (e.g., in a salt form, such as a sulfate salt, or a free base form), and phosphate buffer saline. In some embodiments, the therapeutic composition comprises TGF-β1, CTGF, dextrose, chondroitin (e.g., in a salt form, such as a sulfate salt, or a free base form), and water or saline. In some embodiments, the therapeutic composition comprises TGF-β1, CTGF, dextrose, carboxymethyl cellulose (e.g., in an acid form or a salt form, such as a sodium salt), and glucosamine (e.g., in a free base or a salt form, such as an HCl salt). In some embodiments, the therapeutic composition comprises TGF-β1, CTGF, dextrose, carboxymethyl cellulose (e.g., in an acid form or a salt form, such as a sodium salt), and hyaluronic acid (e.g., in an acid form or a salt form, such as a sodium salt). In some embodiments, the therapeutic composition comprises TGF-β1, CTGF, dextrose, carboxymethyl cellulose (e.g., in an acid form or a salt form, such as a sodium salt), and phosphate buffer saline. In some embodiments, the therapeutic composition comprises TGF-β1, CTGF, dextrose, carboxymethyl cellulose (e.g., in an acid form or a salt form, such as a sodium salt), and water or saline. In some embodiments, the therapeutic composition comprises TGF-β1, CTGF, dextrose, glucosamine (e.g., in a free base or a salt form, such as an HCl salt), and hyaluronic acid (e.g., in an acid form or a salt form, such as a sodium salt). In some embodiments, the therapeutic composition comprises TGF-β1, CTGF, dextrose, glucosamine (e.g., in a free base or a salt form, such as an HCl salt), and phosphate buffer saline. In some embodiments, the therapeutic composition comprises TGF-β1, CTGF, dextrose, glucosamine (e.g., in a free base or a salt form, such as an HCl salt), and water or saline. In some embodiments, the therapeutic composition comprises TGF-β1, CTGF, dextrose, hyaluronic acid (e.g., in an acid form or a salt form, such as a sodium salt), and phosphate buffer saline. In some embodiments, the therapeutic composition comprises TGF-β1, CTGF, dextrose, hyaluronic acid (e.g., in an acid form or a salt form, such as a sodium salt), and water or saline. In some embodiments, the therapeutic composition comprises TGF-β1, CTGF, dextrose, phosphate buffer saline, and water or saline. In some embodiments, the therapeutic composition comprises TGF-β1, CTGF, a local anesthetic such as lidocaine (either in a free base form or a salt form), chondroitin (e.g., in a salt form, such as a sulfate salt, or a free base form), and carboxymethyl cellulose (e.g., in an acid form or a salt form, such as a sodium salt). In some embodiments, the therapeutic composition comprises TGF-β1, CTGF, a local anesthetic such as lidocaine (either in a free base form or a salt form), chondroitin (e.g., in a salt form, such as a sulfate salt, or a free base form), and glucosamine (e.g., in a free base or a salt form, such as an HCl salt). In some embodiments, the therapeutic composition comprises TGF-β1, CTGF, a local anesthetic such as lidocaine (either in a free base form or a salt form), chondroitin (e.g., in a salt form, such as a sulfate salt, or a free base form), and hyaluronic acid (e.g., in an acid form or a salt form, such as a sodium salt). In some embodiments, the therapeutic composition comprises TGF-β1, CTGF, a local anesthetic such as lidocaine (either in a free base form or a salt form), chondroitin (e.g., in a salt form, such as a sulfate salt, or a free base form), and phosphate buffer saline. In some embodiments, the therapeutic composition comprises TGF-β1, CTGF, a local anesthetic such as lidocaine (either in a free base form or a salt form), chondroitin (e.g., in a salt form, such as a sulfate salt, or a free base form), and water or saline. In some embodiments, the therapeutic composition comprises TGF-β1, CTGF, a local anesthetic such as lidocaine (either in a free base form or a salt form), carboxymethyl cellulose (e.g., in an acid form or a salt form, such as a sodium salt), and glucosamine (e.g., in a free base or a salt form, such as an HCl salt). In some embodiments, the therapeutic composition comprises TGF-β1, CTGF, a local anesthetic such as lidocaine (either in a free base form or a salt form), carboxymethyl cellulose (e.g., in an acid form or a salt form, such as a sodium salt), and hyaluronic acid (e.g., in an acid form or a salt form, such as a sodium salt). In some embodiments, the therapeutic composition comprises TGF-β1, CTGF, a local anesthetic such as lidocaine (either in a free base form or a salt form), carboxymethyl cellulose (e.g., in an acid form or a salt form, such as a sodium salt), and phosphate buffer saline. In some embodiments, the therapeutic composition comprises TGF-β1, CTGF, a local anesthetic such as lidocaine (either in a free base form or a salt form), carboxymethyl cellulose (e.g., in an acid form or a salt form, such as a sodium salt), and water or saline. In some embodiments, the therapeutic composition comprises TGF-β1, CTGF, a local anesthetic such as lidocaine (either in a free base form or a salt form), glucosamine (e.g., in a free base or a salt form, such as an HCl salt), and hyaluronic acid (e.g., in an acid form or a salt form, such as a sodium salt). In some embodiments, the therapeutic composition comprises TGF-β1, CTGF, a local anesthetic such as lidocaine (either in a free base form or a salt form), glucosamine (e.g., in a free base or a salt form, such as an HCl salt), and phosphate buffer saline. In some embodiments, the therapeutic composition comprises TGF-β1, CTGF, a local anesthetic such as lidocaine (either in a free base form or a salt form), glucosamine (e.g., in a free base or a salt form, such as an HCl salt), and water or saline. In some embodiments, the therapeutic composition comprises TGF-β1, CTGF, a local anesthetic such as lidocaine (either in a free base form or a salt form), hyaluronic acid (e.g., in an acid form or a salt form, such as a sodium salt), and phosphate buffer saline. In some embodiments, the therapeutic composition comprises TGF-β1, CTGF, a local anesthetic such as lidocaine (either in a free base form or a salt form), hyaluronic acid (e.g., in an acid form or a salt form, such as a sodium salt), and water or saline. In some embodiments, the therapeutic composition comprises TGF-β1, CTGF, a local anesthetic such as lidocaine (either in a free base form or a salt form), phosphate buffer saline, and water or saline. In some embodiments, the therapeutic composition comprises TGF-β1, CTGF, chondroitin (e.g., in a salt form, such as a sulfate salt, or a free base form), carboxymethyl cellulose (e.g., in an acid form or a salt form, such as a sodium salt), and glucosamine (e.g., in a free base or a salt form, such as an HCl salt). In some embodiments, the therapeutic composition comprises TGF-β1, CTGF, chondroitin (e.g., in a salt form, such as a sulfate salt, or a free base form), carboxymethyl cellulose (e.g., in an acid form or a salt form, such as a sodium salt), and hyaluronic acid (e.g., in an acid form or a salt form, such as a sodium salt). In some embodiments, the therapeutic composition comprises TGF-β1, CTGF, chondroitin (e.g., in a salt form, such as a sulfate salt, or a free base form), carboxymethyl cellulose (e.g., in an acid form or a salt form, such as a sodium salt), and phosphate buffer saline. In some embodiments, the therapeutic composition comprises TGF-β1, CTGF, chondroitin (e.g., in a salt form, such as a sulfate salt, or a free base form), carboxymethyl cellulose (e.g., in an acid form or a salt form, such as a sodium salt), and water or saline. In some embodiments, the therapeutic composition comprises TGF-β1, CTGF, chondroitin (e.g., in a salt form, such as a sulfate salt, or a free base form), glucosamine (e.g., in a free base or a salt form, such as an HCl salt), and hyaluronic acid (e.g., in an acid form or a salt form, such as a sodium salt). In some embodiments, the therapeutic composition comprises TGF-β1, CTGF, chondroitin (e.g., in a salt form, such as a sulfate salt, or a free base form), glucosamine (e.g., in a free base or a salt form, such as an HCl salt), and phosphate buffer saline. In some embodiments, the therapeutic composition comprises TGF-β1, CTGF, chondroitin (e.g., in a salt form, such as a sulfate salt, or a free base form), glucosamine (e.g., in a free base or a salt form, such as an HCl salt), and water or saline. In some embodiments, the therapeutic composition comprises TGF-β1, CTGF, chondroitin (e.g., in a salt form, such as a sulfate salt, or a free base form), hyaluronic acid (e.g., in an acid form or a salt form, such as a sodium salt), and phosphate buffer saline. In some embodiments, the therapeutic composition comprises TGF-β1, CTGF, chondroitin (e.g., in a salt form, such as a sulfate salt, or a free base form), hyaluronic acid (e.g., in an acid form or a salt form, such as a sodium salt), and water or saline. In some embodiments, the therapeutic composition comprises TGF-β1, CTGF, chondroitin (e.g., in a salt form, such as a sulfate salt, or a free base form), phosphate buffer saline, and water or saline. In some embodiments, the therapeutic composition comprises TGF-β1, CTGF, carboxymethyl cellulose (e.g., in an acid form or a salt form, such as a sodium salt), glucosamine (e.g., in a free base or a salt form, such as an HCl salt), and hyaluronic acid (e.g., in an acid form or a salt form, such as a sodium salt). In some embodiments, the therapeutic composition comprises TGF-β1, CTGF, carboxymethyl cellulose (e.g., in an acid form or a salt form, such as a sodium salt), glucosamine (e.g., in a free base or a salt form, such as an HCl salt), and phosphate buffer saline. In some embodiments, the therapeutic composition comprises TGF-β1, CTGF, carboxymethyl cellulose (e.g., in an acid form or a salt form, such as a sodium salt), glucosamine (e.g., in a free base or a salt form, such as an HCl salt), and water or saline. In some embodiments, the therapeutic composition comprises TGF-β1, CTGF, carboxymethyl cellulose (e.g., in an acid form or a salt form, such as a sodium salt), hyaluronic acid (e.g., in an acid form or a salt form, such as a sodium salt), and phosphate buffer saline. In some embodiments, the therapeutic composition comprises TGF-β1, CTGF, carboxymethyl cellulose (e.g., in an acid form or a salt form, such as a sodium salt), hyaluronic acid (e.g., in an acid form or a salt form, such as a sodium salt), and water or saline. In some embodiments, the therapeutic composition comprises TGF-β1, CTGF, carboxymethyl cellulose (e.g., in an acid form or a salt form, such as a sodium salt), phosphate buffer saline, and water or saline. In some embodiments, the therapeutic composition comprises TGF-β1, CTGF, glucosamine (e.g., in a free base or a salt form, such as an HCl salt), hyaluronic acid (e.g., in an acid form or a salt form, such as a sodium salt), and phosphate buffer saline. In some embodiments, the therapeutic composition comprises TGF-β1, CTGF, glucosamine (e.g., in a free base or a salt form, such as an HCl salt), hyaluronic acid (e.g., in an acid form or a salt form, such as a sodium salt), and water or saline. In some embodiments, the therapeutic composition comprises TGF-β1, CTGF, glucosamine (e.g., in a free base or a salt form, such as an HCl salt), phosphate buffer saline, and water or saline.

In some embodiments, the therapeutic composition comprises TGF-β1, CTGF, a local anesthetic such as lidocaine (either in a free base form or a salt form), chondroitin (e.g., in a salt form, such as a sulfate salt, or a free base form), carboxymethyl cellulose (e.g., in an acid form or a salt form, such as a sodium salt), glucosamine (e.g. in a free base or a salt form, such as an HCl salt), hyaluronic acid (e.g. in an acid form or a salt form, such as a sodium salt), phosphate buffer saline, and water or saline. In some embodiments, the therapeutic composition comprises TGF-β1, CTGF, dextrose, chondroitin (e.g., in a salt form, such as a sulfate salt, or a free base form), carboxymethyl cellulose (e.g., in an acid form or a salt form, such as a sodium salt), glucosamine (e.g., in a free base or a salt form, such as an HCl salt), hyaluronic acid (e.g., in an acid form or a salt form, such as a sodium salt), phosphate buffer saline, and water or saline. In some embodiments, the therapeutic composition comprises TGF-β1, CTGF, dextrose, a local anesthetic such as lidocaine (either in a free base form or a salt form), carboxymethyl cellulose (e.g., in an acid form or a salt form, such as a sodium salt), glucosamine (e.g., in a free base or a salt form, such as an HCl salt), hyaluronic acid (e.g., in an acid form or a salt form, such as a sodium salt), phosphate buffer saline, and water or saline. In some embodiments, the therapeutic composition comprises TGF-β1, CTGF, dextrose, a local anesthetic such as lidocaine (either in a free base form or a salt form), chondroitin (e.g., in a salt form, such as a sulfate salt, or a free base form), glucosamine (e.g., in a free base or a salt form, such as an HCl salt), hyaluronic acid (e.g., in an acid form or a salt form, such as a sodium salt), phosphate buffer saline, and water or saline. In some embodiments, the therapeutic composition comprises TGF-β1, CTGF, dextrose, a local anesthetic such as lidocaine (either in a free base form or a salt form), chondroitin (e.g., in a salt form, such as a sulfate salt, or a free base form), carboxymethyl cellulose (e.g., in an acid form or a salt form, such as a sodium salt), hyaluronic acid (e.g., in an acid form or a salt form, such as a sodium salt), phosphate buffer saline, and water or saline. In some embodiments, the therapeutic composition comprises TGF-β1, CTGF, dextrose, a local anesthetic such as lidocaine (either in a free base form or a salt form), chondroitin (e.g., in a salt form, such as a sulfate salt, or a free base form), carboxymethyl cellulose (e.g., in an acid form or a salt form, such as a sodium salt), glucosamine (e.g., in a free base or a salt form, such as an HCl salt), phosphate buffer saline, and water or saline. In some embodiments, the therapeutic composition comprises TGF-β1, CTGF, dextrose, a local anesthetic such as lidocaine (either in a free base form or a salt form), chondroitin (e.g., in a salt form, such as a sulfate salt, or a free base form), carboxymethyl cellulose (e.g., in an acid form or a salt form, such as a sodium salt), glucosamine (e.g., in a free base or a salt form, such as an HCl salt), hyaluronic acid (e.g. in an acid form or a salt form, such as a sodium salt), and water or saline. In some embodiments, the therapeutic composition comprises TGF-β1, CTGF, dextrose, a local anesthetic such as lidocaine (either in a free base form or a salt form), chondroitin (e.g., in a salt form, such as a sulfate salt, or a free base form), carboxymethyl cellulose (e.g., in an acid form or a salt form, such as a sodium salt), glucosamine (e.g., in a free base or a salt form, such as an HCl salt), hyaluronic acid (e.g., in an acid form or a salt form, such as a sodium salt), and phosphate buffer saline.

In some embodiments, the therapeutic composition comprises TGF-β1, CTGF, chondroitin (e.g., in a salt form, such as a sulfate salt, or a free base form), carboxymethyl cellulose (e.g., in an acid form or a salt form, such as a sodium salt), and glucosamine (e.g., in a free base or a salt form, such as an HCl salt).

In some embodiments, the therapeutic composition comprises TGF-β1, CTGF, chondroitin (e.g., in a salt form, such as a sulfate salt, or a free base form), glucosamine (e.g., in a free base or a salt form, such as an HCl salt), and phosphate buffer saline.

In some embodiments, the therapeutic composition comprises TGF-β1, CTGF, dextrose, chondroitin (e.g., in a salt form, such as a sulfate salt, or a free base form), and glucosamine (e.g., in a free base or a salt form, such as an HCl salt).

In some embodiments, the therapeutic composition comprises TGF-β1, CTGF, chondroitin (e.g., in a salt form, such as a sulfate salt, or a free base form), carboxymethyl cellulose (e.g., in an acid form or a salt form, such as a sodium salt), glucosamine (e.g., in a free base or a salt form, such as an HCl salt), and phosphate buffer saline.

In some embodiments, the therapeutic composition comprises TGF-β1, CTGF, dextrose, chondroitin (e.g., in a salt form, such as a sulfate salt, or a free base form), glucosamine (e.g., in a free base or a salt form, such as an HCl salt), and phosphate buffer saline.

In some embodiments, the therapeutic composition comprises TGF-β1, CTGF, dextrose, chondroitin (e.g., in a salt form, such as a sulfate salt, or a free base form), carboxymethyl cellulose (e.g., in an acid form or a salt form, such as a sodium salt), and glucosamine (e.g., in a free base or a salt form, such as an HCl salt).

In some embodiments, the therapeutic composition comprises TGF-β1, CTGF, dextrose, chondroitin (e.g., in a salt form, such as a sulfate salt, or a free base form), carboxymethyl cellulose (e.g., in an acid form or a salt form, such as a sodium salt), glucosamine (e.g., in a free base or a salt form, such as an HCl salt), and phosphate buffer saline.

In some embodiments, the therapeutic composition comprises:
1. Transforming growth factor beta 1 (TGF-β1) 5 ng/mL to 100 ng/mL;
2. Connective tissue growth factor (CTGF) 50 ng/mL to 200 ng/mL;
3. Dextrose 0%-25%;
4. Chondroitin sulfate 0.5%-2%
5. Carboxymethyl cellulose 0-0.5%
6. Glucosamine HCL 1%-25%
7. Hyaluronic acid 0.05%-6%
8. Phosphate buffer salines, pH ~7-8
9. Water QS (sterile water or normal saline QS)

Unless otherwise indicated, all numbers expressing quantities of ingredients, properties such as amounts, percentage, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the embodiments (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the embodiments and does not pose a limitation on the scope of any claim. No language in the specification should be construed as indicating any non-claimed element essential to the practice of the claims.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or to expedite prosecution. When any such inclusion or deletion occurs, the specification is deemed to contain the group as modified thus fulfilling the written description of all Markush groups if used in the appended claims.

Certain embodiments are described herein, including the best mode known to the inventors for carrying out the claimed embodiments. Of course, variations on these described embodiments will become apparent to those of ordinary skill in the art upon reading the foregoing description. The inventor expects skilled artisans to employ such variations as appropriate, and the inventors intend for the claimed embodiments to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A method of treating a connective tissue injury, comprising injecting a therapeutic composition into a fibro-periosteal junction of an injured connective tissue in an animal in need thereof, wherein the therapeutic composition comprises transforming growth factor beta 1 (TGF-β1), connective tissue growth factor (CTGF), and a pharmaceutically acceptable excipient or a secondary agent, wherein the connective tissue injury is a result of an automobile collision, a sports injury, or other trauma.

2. The method of claim 1, wherein the animal is a human being.

3. The method of claim 1, wherein the therapeutic composition is injected into a fibro-periosteal junction of a tendon of the animal.

4. The method of claim 1, wherein the therapeutic composition is injected into a fibro-periosteal junction of a fascia of the animal.

5. The method of claim 1, wherein the therapeutic composition is injected into a fibro-periosteal junction of a ligament of the animal.

6. The method of claim 1, wherein the therapeutic composition is injected into a fibro-periosteal junction of a joint capsule of the animal.

7. The method of claim 1, wherein the pharmaceutically acceptable excipient or the secondary agent comprises glucosamine.

8. The method of claim 1, wherein the pharmaceutically acceptable excipient or the secondary agent comprises chondroitin.

9. The method of claim 1, wherein the pharmaceutically acceptable excipient or the secondary agent comprises dextrose.

10. The method of claim 1, wherein the pharmaceutically acceptable excipient or the secondary agent comprises a local anesthetic.

11. The method of claim 1, wherein the pharmaceutically acceptable excipient or the secondary agent comprises carboxymethyl cellulose.

12. The method of claim 1, wherein the pharmaceutically acceptable excipient or the secondary agent comprises hyaluronic acid.

13. The method of claim 1, wherein the pharmaceutically acceptable excipient or the secondary agent comprises a phosphate buffer saline.

* * * * *